United States Patent [19]

Hopkins, II et al.

[11] 4,104,030

[45] Aug. 1, 1978

[54] PHOTOMETRIC DETERMINATION OF PROTEIN, AND OF ENDOTOXIN WITH LIMULUS PROTEIN

[75] Inventors: Robert E. Hopkins, II, Morton Grove; Kathleen Hughes, Des Plaines, both of Ill.

[73] Assignee: Baxter Travenol Laboratories, Inc., Deerfield, Ill.

[21] Appl. No.: 848,628

[22] Filed: Nov. 4, 1977

[51] Int. Cl.² .................. G01N 33/16; G01N 21/06
[52] U.S. Cl. ..................... 23/230 B; 195/103.5 R; 252/408; 260/112 R; 424/2
[58] Field of Search .............. 23/230 B; 195/103.5 R; 252/408; 260/112 R; 424/2

[56] References Cited

U.S. PATENT DOCUMENTS

| | | | |
|---|---|---|---|
| 2,897,058 | 7/1959 | Goldt | 23/230 B |
| 3,558,278 | 1/1971 | Louderback | 23/230 B |
| 3,873,272 | 3/1975 | Wakefield | 23/230 B |
| 3,884,637 | 5/1975 | Gindler | 23/230 B |
| 3,915,805 | 10/1975 | Levin | 23/230 B X |
| 3,944,391 | 3/1976 | Harris | 195/103.5 R X |
| 3,954,663 | 5/1976 | Yamamoto | 195/103.5 R X |
| 4,023,933 | 5/1977 | Bradford | 23/230 B |
| 4,038,029 | 7/1977 | Teller | 195/103.5 R X |
| 4,038,147 | 7/1977 | Reno | 195/103.5 R |

OTHER PUBLICATIONS

R. Nandan et al., J. Lab. Clin. Med., 89 (4), 910–918, Apr. 1977.
Chemical Abstracts, 84:145808p (1976).
Chemical Abstracts, 84:155680e (1976).

*Primary Examiner*—Sidney Marantz
*Attorney, Agent, or Firm*—Paul C. Flattery; Lawrence W. Flynn; Max D. Hensley

[57] ABSTRACT

An optical density technique for measuring protein concentration generally, or for measuring minute traces of endotoxin in an unknown material by the clotting of Limulus lysate protein. After the clotting step, the clotted protein is separated and digested in from 0.1 to 0.4N strong alkali such as sodium hydroxide and then photometrically analyzed, for example with the Lowry test. Greatly improved stability of a quantitative endpoint is achieved under this circumstance.

6 Claims, No Drawings

PHOTOMETRIC DETERMINATION OF PROTEIN, AND OF ENDOTOXIN WITH LIMULUS PROTEIN

In the Nandan U.S. Pat. applicaton Ser. No. 465,990 filed May 1, 1974, an improved method for detecting minute traces of endotoxin by the use of a photometric analytical technique of clotted Limulus protein is disclosed. The method is approximaately eight times more sensitive than the conventional clot-type analytical technique. Another description of this method is found in the article by R. Nandan and D. Brown entitled "*A New In Vitro Pyrogen Test: To Detect picograms of Endotoxin Contamination in Intravenous Fluids Using Limulus Amoebocyte Lysate*", *J. Lab. Clin. Med.*, Vol. 89, No. 4, pp. 910–918 (April, 1977).

Basicaly, the Limulus lysate protein is brought into contact with the unknown material which, in the presence of picogram quantities of bacterial endotoxin, results in the formation of a precipitate of at least some of the Limulus protein present. The precipitate is centrifuged, and the supernatant, containing unprecipitated Limulus protein, is decanted.

Thereafter, the precipitated Limulus protein is redissolved, conventionally in 0.75N sodium hydroxide solution. Then, the concentration of protein present is determined against a serially diluted standard endotoxin curve by means of the well-known Lowry protein test, to quantitatively determine the amount of precipitated protein, which, in turn, is a function of the endotoxin concentration as indicated by the standard curve.

The well-known Lowry test for protein is, for example, discussed in the textbook edited by Richard J. Henry entitled *Clinical Chemistry, Principles and Techniques*, p.p. 424–425, Harper and Row (Second Edition, 1974) (plus the footnote references). According to this reference, Folin and Denis found that a phosphotungstic-phosphomolybidic acid reagent gives a blue color with proteins and certain other compounds. The process was improved as a means for protein detection by substituting lithium salts for sodium salts, particularly by means of the Folin-Ciocalteu reagent.

As a further improvement to the process, the protein is conventionally pretreated with an alkaline copper solution (typically 0.1N sodium hydroxide solution), which pretreatment has been found to greatly increase the sensitivity of the reaction to protein. The color produced reportedly results from the reduction of the phosphotungstic-phosphomolybidic acids by the copper protein complex and certain amino acids present in most proteins. The Lowry test is based on this.

The above is the technology which can be improved by the method of this invention. The colored materials described above are broadly intended to be incorporated by the term "Lowry-type protein-indicating complex" as used in the claims below.

Also, while it is preferred to use the method of this application in conjunction with Limulus lysate proteins, the similar endotoxin-clottable proteins of other crab species are also particularly preferred for use herein.

It has been found that the Lowry-type protein-indicating complex, as treated by prior art techniques, is rather unstable, which results in an endpoint of short duration in quantitative photometric tests using Lowry protein methods. For example, in one test involving an endotoxin concentration of 200 picograms of endotoxin, after five minutes the reaction solution exhibited an absorbence of slightly above 0.9, but after the prescribed test incubation time of thirty minutes the absorbence had spontaneously declined to about 0.7.

When a protein testing method is contemplated for large-scale industrial use, it is of course undesirable to utilize a test having an unstable endpoint, since the test will be performed on a repeated and large scale basis, and delays in the final analysis may be inevitable.

Accordingly, there is a need for a photometric protein test which exhibits the extreme sensitivity of the test as described in the Nandan, et al. patent application and article, while at the same time providing improved stability of the reaction mixture at its endpoint.

In accordance with this invention, it has been found that a reduction in the amount of strong alkali which is used to dissolve the precipitated protein in a protein analysis such as the process described above, prior to photometric analysis, provides a very significant increase in the stability of the endpoint, so that essentially the maximum optical density reading will remain available in the reaction mixture for a more extended period of time. Particularly it is preferred for such strong alkali to be present in a concentration of 0.1 to 0.4N, the specific concentration being selected by the user to achieve the desired timing of the endpoint.

At the lower concentrations of strong alkali within the above preferred range, there may be an initial period after mixing the Lowry test reactants, during which the optical density rises. After a short period, depending upon the concentration of the strong alkali used to redissolve the protein precipitate, the optical density of the photometric test, which of course is a function of the amount of redissolved protein precipitate present, reaches an extended maximum. This maximum remains for an increased period of time, facilitating the careful analysis of the test, and also permitting repetitions of the analytical step where desired.

Thereafter, as in tests where higher alkali concentrations are used to digest the protein, there is a slow deterioration of the complex indicating the presence of protein in the Lowry test, with a resultant reduction of optical density.

Accordingly, in a preferred process of this invention, Limulus lysate is added to an unknown material, and the resulting precipitate is collected, preferably by centrifugation, with the supernatant being decanted or removed with a pipette, as desired. Thereafter, the precipitate is redissolved in strong alkali, for example sodium hydroxide solution in a concentration of 0.1 to 0.4N.

The resulting test mixture is then photometrically analyzed, preferably using a Lowry protein technique as described in the above-cited article, for comparison against a standard curve of similarly-treated, serially diluted endotoxin solutions, in order to obtain a stable, long endpoint during which the maximum optical density can be measured, and then compared with the standard curve to determine the presence of endotoxin in the unknown material.

Also it is contemplated that the invention of this application may be used with other protein tests, for example for quantitative analysis of human serum albumin in a quantitative manner by first digesting the human serum albumin in sodium hydroxide solution having a concentration of 0.1 to 0.4N, and then subjecting the resulting digested solution to a Lowry-type analysis in order to obtain a quantitative photometric endpoint. The process may be utilized with any other protein as well which is digestible in sodium hydroxide solution of the preferred concentration range.

While sodium hydroxide is one preferred strong alkali for use herein, it is also contemplated that other alkali metal hydroxides such as potassium hydroxide or caesium hydroxide can be used, and that strong quaternary ammonium hydroxides such as tetraethyl ammonium hydroxide can also be used. Weaker alkali materials having an equivalent hydroxyl ion concentration to 0.1 to 0.4N sodium hydroxide solution can also be used as an alternative, if desired.

The following examples are for illustrative purposes only, and are not intended to limit the invention of this application, which is as defined in the claims below.

EXAMPLE 1

Pyrogens present in all glassware and utilized in this example were removed by dry heat in an oven at 250° C. for 4 hours. Tests were carried out in sterile, pyrogen-free culture test tubes which were covered with plastic material immediately after the reactants were added in order to prevent air-borne contamination.

A. This particular experiment was to show the typical behavior of the Lowry-type protein test at its endpoint as utilized by Nandan and Brown, as reported by the previously-cited article, using a modification of Lowry's method for total protein as described in Lowry, et al. *J. Biol. Chem.* 193:265–275 (1951).

REAGENTS

All reagents were prepared in distilled water.

Lowry Copper Reagent: Stock solution [5 g. of $CuSO_2.5H_2O$ in 1 liter of 0.085N potassium sodium tartrate.]

Sodium Carbonate, Stock solution: (2 g. $Na_2CO_3$ in 100 ml. of 0.1N NaOH).

Working Lowry Copper Reagent: prepared by diluting 2.0 ml. of stock Lowry copper reagent to 100 ml. with stock sodium carbonate solution.

Folin-Ciocalteu Phenol Reagent: (2N solution): sold by Fisher Scientific Company, New Jersey.

Working Folin Reagent was prepared by diluting 1 part of Folin-Ciocalteu Phenol Reagent solution with one part of distilled water.

Sodium Hydroxide 0.75N: prepared by appropriately diluting standardized 10N Sodium Hydroxide, sold by the Fisher Scientific Company.

Human crystallized albumin was obtained from the American Hospital Supply Corporation. The albumin was digested in 0.75N sodium hydroxide solution samples, to provide the following concentrations of albumin in varying samples of the sodium hydroxide solution: 20, 40, 80, and 160 micrograms per 0.2 ml.

0.2 ml. of each of these digested solutions were placed in a culture test tube.

One ml. of Working Lowry Copper Reagent was added to each 0.2 ml. protein solution sample. The mixture was allowed to stand for 10 minutes at room temperature (25° ± 2° C.). At the end of this period 0.1 ml. of Working Folin reagent was added, and the solution mixed immediately.

Multiple samples of each albumin concentraton were prepared, and the absorbance of each mixture was measured as a function of time from final mixing of the ingredients, in a Gilford 300N spectrophotometer at 500 nanometers, with results as follows:

TABLE I

Optical Density of Protein Solutions at Various Protein Concentrations (Micrograms/0.2ml.)

| Time (Min.) | 20 micrograms/.2ml. (2 samples) | | 40 micrograms/.2ml. (2 samples) | | 80 micrograms/.2ml. (2 samples) | | 160 micrograms/.2ml (2 samples) | |
|---|---|---|---|---|---|---|---|---|
| 5 | .144, | .148 | .282, | .280 | .508, | .519 | .911, | .934 |
| 10 | .141, | .141 | .266, | .267 | .486, | .490 | .866, | .867 |
| 15 | .142, | .126 | .242, | .242, | .441, | .447 | .790, | .801 |
| 20 | .116, | .119 | .224, | .218 | .399, | .407 | .736, | .753 |
| 25 | .098, | .100 | .198, | .196 | .356, | .364 | .683, | .680 |
| 30 | .090, | .089 | .172, | .179 | .321, | .319 | .608, | .628 |
| 35 | .078, | .081 | .157, | .152 | .292, | .298 | .575, | .577 |
| 40 | .086, | .072 | .141, | .140 | .253, | .264 | .497, | .520 |

It can be seen that there is severe loss of optical density over a 30 minute period. The loss is significant over even a 10 minute period following mixing of the reagents.

B. The experiment of Example 1A above was repeated, with the exception that the concentration of sodium hydroxide used to digest the albumin was 0.3N rather than 0.75N. Multiple samples of each albumin concentration were prepared, and the absorbance of each mixture was measured as a function of time from the final mixing of the ingredients, in a Gilford 300N spectrophotometer at 500 nanometers, with results as shown in Table II:

TABLE II

Optical Density of Protein Solutions at Various Protein Concentrations (Micrograms/0.2ml.)

| Time (Min.) | 20 micrograms/.2ml. | 40 micrograms/.2ml | 80 micrograms/.2ml. | 160 micrograms/.2ml. |
|---|---|---|---|---|
| 5 | .171 | .308 | .539 | .868 |
| 10 | .171 | .312 | .530 | .858 |
| 15 | .173 | .307 | .526 | .852 |
| 20 | .173 | .306 | .523 | .840 |
| 25 | .172 | .303 | .528 | .829 |
| 30 | .171 | .300 | .510 | .811 |

It can be seen that in the recorded 25 minute period between 5 and 30 minutes after mixing of the reagents, the optical density value decreased by less than 10 percent in all cases. This is to be compared with a decrease in optical density in the same period of time of between 30 and 40 percent in the previous Example 1A.

C. The experiment of Example 1A was repeated, except that the concentration of sodium hydroxide solution used to digest the albumin was 0.4N rather than 0.75N.

As before, multiple samples of each albumin concentration were prepared, and the absorbance of each mixture was measured in the same manner as previously described, with results as shown in Table III:

TABLE III

Optical Density of Protein Solutions at Various Protein Concentrations (Micrograms/0.2ml.)

| Time (Min.) | 20 micrograms/.2ml. | 40 micrograms/.2ml. | 80 micrograms/.2ml. | 160 micrograms/.2ml. |
|---|---|---|---|---|
| 5 | .158 | .277 | .485 | .805 |
| 10 | .152 | .272 | .480 | .796 |
| 15 | .153 | .277 | .474 | .786 |
| 20 | .150 | .271 | .465 | .771 |
| 25 | .149 | .258 | .455 | .752 |
| 30 | .149 | .252 | .441 | .724 |

It can be seen that in this example also that the deterioration of the optical density between 5 and 30 minutes is no more than about 10 percent, in contrast to the very substantial degradation over the similar period as shown under the conditions of Example 1A.

Generally equivalent results are achieved when the experiment of this Example 1C is repeated utilizing the well-known Oyama-Eagle method for photometrically determining protein concentrations (Oyama, V. I. and Eagle, H. "*Measurement of Cell Growth in Tissue Culture With a Phenol Reagent (Folin-Ciocalteau)*", *Proc. Soc. Exptl. Biol. Med.*, 91:305–307 (1956) with a deterioration in the optical density between over 5 and 30 minutes being generally less than 10 percent.

D. The experiment of Example 1A was repeated except that the sodium hydroxide concentration used to digest the albumin precipitate was 0.25N rather than 0.75N. Multiple samples of each albumin concentration were prepared, and the absorbance of each mixture was measured in the manner previously described, with results as shown in Table IV:

TABLE IV

| | Optical Density of Protein Solutions at Various Protein Concentrations (Micrograms/0.2ml.) | | |
|---|---|---|---|
| Time (Min.) | 20 micrograms/.2ml. | 40 micrograms/.2ml. | 160 micrograms/.2ml |
| 5 | .168 | .302 | .884 |
| 10 | .167 | .300 | .876 |
| 15 | .170 | .303 | .875 |
| 20 | .171 | .302 | .875 |
| 25 | .172 | .303 | .872 |
| 30 | .173 | .303 | .882 |

Under these reaction conditions it can be seen that over the period from 5 to 30 minutes there is little or no significant deterioration in optical density. The deviations in optical density which are present are attributed primarily to the normal statistical deviation of the experimental results.

E. The experiment of Example 1A was repeated, except that 0.2N sodium hydroxide was used to digest the albumin protein rather than the 0.75N sodium hydroxide solution.

Multiple samples of each albumin concentration were prepared, and the absorbance of each mixture was measured in the manner previously described, with results as shown in Table V.

TABLE V

| | Optical Density of Protein Solutions at Various Protein Concentrations (Micrograms/0.2ml.) | | | |
|---|---|---|---|---|
| Time (Min.) | 20 micrograms/.2ml. | 40 micrograms/.2ml. | 80 micrograms/.2ml. | 160 micrograms/.2ml. |
| 5 | .167 | .306 | .537 | .861 |
| 10 | .182 | .332 | .583 | .943 |
| 15 | .193 | .349 | .607 | .959 |
| 20 | .199 | .354 | .608 | .959 |
| 25 | .197 | .352 | .607 | .957 |
| 30 | .198 | .355 | .607 | .954 |

Under these reaction conditions, it is desirable to wait at least about 15 minutes after mixing of the reagents prior to making the photometric reading of protein concentration, because the optical density rises to its maximum over a period of time approximating 15 minutes, indicating that the reaction has not gone to completion until then. The reaction mixture then remains stable for an extended period of time after that, and thus is a useful reaction system when maintenance of the reaction mixture over an extended period of time is desired.

F. The experiment of Example 1A was again repeated, but utilizing 0.1N sodium hydroxide solution to digest the albumin protein, rather than 0.75N solution.

Multiple samples of each albumin concentration were prepared, and the absorbance of each mixture was measured in the manner previously described, with the results as shown in Table VI.

TABLE VI

| | Optical Density of Protein Solutions at Various Protein Concentrations (Micrograms/.02ml.) | | | |
|---|---|---|---|---|
| Time (Min.) | 20 micrograms/.2ml. | 40 micrograms/.2ml. | 80 micrograms/.2ml. | 160 micrograms/.2ml. |
| 5 | .157 | .289 | .498 | .852 |
| 10 | .164 | .300 | .529 | .907 |
| 15 | .177 | .320 | .562 | .956 |
| 20 | .185 | .337 | .590 | .983 |
| 25 | .192 | .346 | .598 | .985 |
| 30 | .195 | .350 | .602 | .985 |

Under these reaction conditions, the optical density continues to rise toward its maximum for a period of about 30 minutes or more, at which time it tends to level off to provide essentially maximum stability, for careful analysis or storage of the reaction mixture while maintaining the maximum optical density.

Example 2A

Limulus amoebocyte lysate was prepared by lysing the amoebocyte cells in distilled, non-pyrogenic water and filtering insoluble portions from the resulting solution. As in Example 1, all glassware and the like utilized in this Example was made pyrogen-free by dry heat in an oven at 250° C. for 4 hours, and the other precautions described in that example for maintaining sterility were followed. The filtered solution was then lyophilized to dry powder, and 22 to 30 mg. (11 to 13 mg. of protein) portions of the powder were sealed in vials.

For use in this example, each vial was reconstituted to a solution with 3 ml. of 0.5 weight percent aqueous magnesium chloride solution.

0.1 ml. of this solution was mixed with 0.1 ml. of endotoxin solution (Difco *E. Coli* endotoxin). Various concentrations of endotoxin solution were utilized as indicated in Table VII below. The endotoxin lysate mixtures were incubated for 1 hour at 37° C. and then allowed to cool for 5 to 10 minutes.

Thereafter, the endotoxin lysate tubes were centrifuged at 12,100 G. for 10 minutes, with the supernatant being decanted by aspiration. To this was then added 0.2 ml. of 0.75N sodium hydroxide solution.

There was then added to each of the tubes 1 ml. of the Working Lowry Copper Reagent as described in the previous example, with each of the tubes being allowed to stand for 10 minutes at room temperature.

Following this, there was added 0.1 ml. of the Working Folin reagent as described in the previous example with vigorous stirring by the use of a vortex machine. Counting from that time, the optical density was repeatedly measured as in the previous example, but at 660 nanometers with results as follows:

TABLE VII

Optical Density of Limulus Protein Solutions, After Precipitation by Various Concentrations of Endotoxin (Picograms of Endotoxin per ml.)

| Time (Min.) | 200 pg./ml.(Two Samples) | 100 pg./ml.(Two Samples) | 50 pg./ml.(Two Samples) | 12 pg./ml.(Two Samples) | Negative Control (Two Samples) |
|---|---|---|---|---|---|
| 10 | .915, .806 | .616, .635 | .437, .445 | .250, .276 | .233, .171 |
| 15 | .805, .775 | .561, .554 | .420, .435 | .244, .245 | .158, .088 |
| 20 | .696, .733 | .543, .514 | .425, .423 | .206, .213 | .127, .159 |
| 25 | .669, .667 | .509, .505 | .335, .373 | .204, .220 | .107, .140 |
| 30 | .685, .657 | .462, .464 | .293, .310 | .197, .165 | .093, .140 |
| 35 | .668, .561 | .412, .421 | .307, .276 | .164, .171 | .130, .112 |
| 40 | .579, .558 | .392, .413 | .265, .247 | .135, .118 | .239, .095 |

It can be seen that there is a substantial loss of optical density in the period from 10 minutes to 40 minutes after the addition of the working Folin reagent to create the colored material which is indicative of the presence of protein, in accordance with the Lowry test.

B. The experiment of Example 2A was repeated, with the exception that the concentration of sodium hydroxide used to digest the centrifuged protein was 0.25N rather than 0.75N. Multiple samples were prepared with varying concentrations of endotoxin, and the absorbance of each sample was measured as described in Table VIII with the following results:

TABLE VIII

Optical Density of Limulus Protein Solutions, After Precipitation by Various Concentrations of Endotoxin (Picograms of Endotoxin per ml.)

| Time (Min.) | 100 pg./ml. (Two Samples) | 50 pg./ml. (Two Samples) | 12 pg./ml. (Two Samples) | Negative Control (Two Samples) |
|---|---|---|---|---|
| 5 | 1.251, 1.032 | .856, .800 | .365, .370 | .244, .198 |
| 10 | 1.297, 1.328 | .826, .843 | .410, .387 | .231, .266 |
| 15 | 1.273, 1.291 | .864, .855 | .407, .452 | .270, .237 |
| 20 | 1.266, 1.287 | .873, .888 | .507, .420 | .238, .248 |
| 25 | 1.262, 1.295 | .919, .936 | .235, .393 | .239, .255 |
| 30 | 1.237, 1.262 | .919, .913 | .428, .389 | .224, .229 |

It can be seen that the results of this experiment correspond to the similar results of Example 1D with human serum albumin, in which sodium hydroxide solution of a similar concentration of 0.25N was used to digest albumin. In those results, the optical density curves over time remain generally flat over the period from 5 to 30 minutes. In this present experiment, the curve appears to still be rising to a slight degree in at least some instances, in the manner similar to that shown for the more dilute sodium hydroxide digesting solutions in the previous example.

C. The experiment of Example 2A was repeated, with the exception that the concentration of sodium hydroxide used to digest the centrifuged protein was 0.3N rather than 0.75N. Multiple samples were prepared, varying concentrations of endotoxin, and the absorbence of each sample was measured as described in Table IX with the following results:

TABLE IX

Optical Density of Limulus Protein Solutions, After Precipitation by Various Concentrations of Endotoxin (Picograms of Endotoxin per ml.)

| Time (Min.) | 100 pg./ml. (Two Samples) | | 50 pg./ml. (Two Samples) | | 12 pg./ml. (Two Samples) | | Negative Control (Two Samples) | |
|---|---|---|---|---|---|---|---|---|
| 5 | .921 | .938 | .465, | .488 | .259, | .303 | .180, | .189 |
| 10 | .924, | .929 | .484, | .502 | .318, | .286 | .212, | .180 |
| 15 | .924, | .897 | .485, | .483 | .259, | .268 | .200, | .212 |
| 20 | .909, | .923 | .492, | .495 | .305, | .319 | .198, | .203 |
| 25 | .898, | .921 | .482, | .473 | .277, | .271 | .187, | .200 |
| 30 | .924, | .898 | .483, | .516 | .273, | .326 | .184, | .163 |

It can be seen that the optical density curves over time remain generally flat over the period of 5 to 30 minutes, unlike the results of Example 2A utilizing a higher concentration of sodium hydroxide to digest the protein.

That which is claimed is:

1. The method of photometrically determining the presence of protein in an unknown which comprises digesting said protein in an alkali solution equivalent to 0.1 to 0.4N sodium hydroxide, forming a Lowry-type protein-indicating complex with said protein, and photometrically analyzing for the presence of said protein-indicating complex, whereby said protein-indicating complex exhibits an improved stability.

2. The method of claim 1 in which said complex is formed with Folin-Ciocalteu phenol reagent and Lowry copper reagent under alkaline conditions.

3. The method of claim 1 in which said alkali solution is from 0.2 to 0.4N sodium hydroxide solution.

4. In the method of photometrically determining the presence of protein from Limulus lysate in an unknown by forming a Lowry-type protein-indicating complex with said protein under alkaline conditions, and photometrically analyzing for the presence of said protein-indicating complex, the improvement comprising the prior step of digesting said protein in an alkali solution equivalent to 0.1 to 0.4N sodium hydroxide, whereby said protein-indicating complex exhibits an improved stability.

5. The method of claim 1 in which said complex is formed with a Folin-Ciocalteu phenol reagent and a Lowry copper reagent in the presence of an alkali solution equivalent to essentially 0.1N sodium hydroxide.

6. The method of claim 5 in which said alkali solution for digesting the protein is from 0.2 to 0.3N sodium hydroxide solution.

* * * * *

UNITED STATES PATENT AND TRADEMARK OFFICE
CERTIFICATE OF CORRECTION

PATENT NO. : 4,104,030
DATED : August 1, 1978
INVENTOR(S) : Robert E. Hopkins, II and Kathleen Hughes It is certified that error appears in the above-identified patent and that said Letters Patent are hereby corrected as shown below:

In the Abstract, line 8, delete "endopoint" and insert therefor -- endpoint --.

Column 1, line 18, delete "Basicaly," and insert therefor -- Basically, --.

Column 7, line 34, delete ".244" and insert therefor -- .224 --;
line 38, delete ".239" and insert therefor -- .238 --.

Signed and Sealed this

Twenty-second Day of May 1979

[SEAL]

Attest:

RUTH C. MASON
Attesting Officer

DONALD W. BANNER
Commissioner of Patents and Trademarks